United States Patent [19]

Boisvenue

[11] 4,421,759

[45] Dec. 20, 1983

[54] METHODS FOR CONTROLLING FIRE ANTS

[75] Inventor: Rudolph J. Boisvenue, Greenfield, Ind.

[73] Assignee: Eli Lilly and Company, Indianapolis, Ind.

[21] Appl. No.: 286,728

[22] Filed: Jul. 27, 1981

[51] Int. Cl.$^3$ .................. A01N 43/50; A01N 43/56
[52] U.S. Cl. .................... 424/273 R; 424/245; 424/273 B; 424/DIG. 11
[58] Field of Search .................. 424/273 R, DIG. 11, 424/273 B, 245

[56] References Cited

U.S. PATENT DOCUMENTS

| | | | |
|---|---|---|---|
| 3,725,554 | 4/1973 | Burton et al. | 424/273 |
| 3,755,346 | 8/1973 | Soper | 260/309.2 |
| 3,980,784 | 9/1976 | Peterson | 424/273 |
| 3,988,465 | 10/1976 | Röchling et al. | 424/273 |
| 4,122,184 | 10/1978 | Soper | 424/273 |
| 4,191,768 | 3/1980 | Drabb, Jr. et al. | 424/273 R |
| 4,265,901 | 5/1981 | O'Doherty | 424/273 |

FOREIGN PATENT DOCUMENTS

80/2490 2/1981 Zaire .
258/80 4/1981 Zimbabwe .

OTHER PUBLICATIONS

Poster Session at Society of Toxicology Meeting at Washington, D. C. Mar. 10, 1980, "Disposition of a New Ectoparasitic Agent in the Rat," van Lier et al. *Experientia* 36, 189 (1980).
"Trip Report" prepared by Dr. Edgar W. Day as to the content of his presentation at the same meeting.
Outline of oral publication delivered by Dr. Edgar W. Day, on Jul. 8, 1980 to the USDA Fire Ant Working Group Meeting at USDA Laboratory at Gainesville, Florida.
*Southwestern Entomologist*, 4, #4, 311 (Dec. 1979).
Pending application Serial No. 174,371, filed Aug. 1, 1980.
*Farm Chemicals*, Jul. 1980, 29-31.
Outline of oral publication delivered by Dr. Edgar W. Day, on Jan. 30, 1980, to the USDA Fire Ant Working Group Meeting at USDA Animal & Plant Health Inspection Service at Gulfport, Miss.
Boisvenue et al., *Experientia*, 36 (1980) pp. 189-190.
Lofgren et al., (I) Journal of Economic Entomology, vol. 57 (1964) #2, pp. 235-237.
Lofgren et al., (II), Journal of Economic Entomology, vol. 57 (1964) #4, pp. 601-602.

[57] ABSTRACT

This invention is directed to the use of certain benzimidazoles and benzimidazolines as an agent for the control of colonial insects, especially fire ants.

15 Claims, No Drawings

METHODS FOR CONTROLLING FIRE ANTS

BRIEF SUMMARY

This invention is directed to the use of a class of 2-(α,α-difluoroalkyl)benzimidazoles and benzimidazolines as an agent for the control of certain colonial insects, i.e., ants and termites.

DETAILED DESCRIPTION OF THE INVENTION

The present invention is directed to a method for eradicating a colonial insect colony comprised of insects of the order Hymenoptera, family Formicidae, or the order Isoptera, family Termitidae, which comprises supplying to the colony an effective amount of an active agent, the active agent being one or more compounds of the class of 2-(α,α-difluoroalkyl)benzimidazoles of the formula

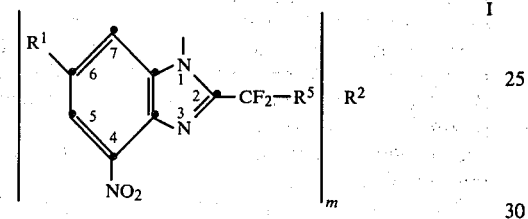

and 2-(α,α-difluoroalkyl)benzimidazolines of the formula

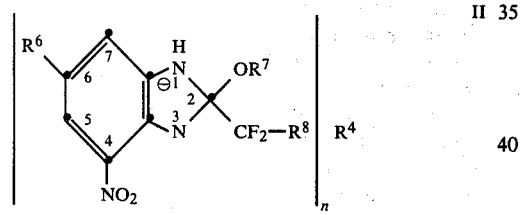

wherein $R^1$–$R^8$ and m and n have the following meanings:

$R^1$ = halo, $CF_3$, $CF_2H$, or $CF_2Cl$;
$R^2$ = H, $COOR^3$, or $R^4$;
$R^3$ = alkyl of $C_1$–$C_8$, alkenyl of $C_3$–$C_4$, or benzyl;
$R^4$ = sodium, potassium, lithium, silver, magnesium, barium, strontium, calcium, ammonium, or substituted ammonium derived from an organic amine which is as basic as, or more basic than, ammonia;
$R^5$ = H, Cl, F, $CF_2H$, or $CF_3$;
$R^6$ = Br, Cl, or $CF_3$;
$R^7$ = H or lower alkyl of $C_1$–$C_4$;
$R^8$ = H, F, $CF_2H$, or $CF_3$;
m = when $R^2$ = H or $COOR^3$, 1, and when $R^2$ = $R^4$, the valence of $R^4$; and
n = the valence of $R^4$.

Representative compounds to be employed in accordance with the present invention include the following:

2-(trifluoromethyl)-4-nitro-6-chlorobenzimidazole
2,6-bis(trifluoromethyl)-4-nitrobenzimidazole
2-(trifluoromethyl)-4-nitro-6-(difluoromethyl)benzimidazole
2-(pentafluoroethyl)-4-nitro-6-(trifluoromethyl)benzimidazole
2-(1,1,2,2-tetrafluoroethyl)-4-nitro-6-(trifluoromethyl)benzimidazole
2-(1,1,2,2-tetrafluoroethyl)-4-nitro-6-chlorobenzimidazole
2-(1,1,2,2-tetrafluoroethyl)-4-nitro-6-bromobenzimidazole
2-(1,1,2,2-tetrafluoroethyl)-4-nitro-6-(difluoromethyl)benzimidazole
2-(1,1,2,2-tetrafluoroethyl)-4-nitro-6-(chlorodifluoromethyl)benzimidazole
2-(difluoromethyl)-4-nitro-6-(trifluoromethyl)benzimidazole
2-(chlorodifluoromethyl)-4-nitro-6-(trifluoromethyl)benzimidazole
2,6-bis(chlorodifluoromethyl)-4-nitrobenzimidazole
2-(1,1,2,2-tetrafluoroethyl)-4-nitro-6-(trifluoromethyl)benzimidazole, sodium salt
2-(1,1,2,2-tetrafluoroethyl)-4-nitro-6-(trifluoromethyl)benzimidazole, ammonium salt
2-(1,1,2,2-tetrafluoroethyl)-4-nitro-6-(trifluoromethyl)benzimidazole, potassium salt
2,6-bis(trifluoromethyl)-4-nitrobenzimidazole, sodium salt
2,6-bis(trifluoromethyl)-4-nitrobenzimidazole, triethylammonium salt
2-(1,1,2,2-tetrafluoroethyl)-4-nitro-6-(trifluoromethyl)benzimidazole, triethylammonium salt
2-propenyl 2,6-bis(trifluoromethyl)-4-nitro-1-benzimidazolecarboxylate
ethyl 2,6-bis(trifluoromethyl)-4-nitro-1-benzimidazolecarboxylate
n-hexyl 2,6-bis(trifluoromethyl)-4-nitro-1-benzimidazolecarboxylate
isopropyl 2,6-bis(trifluoromethyl-4-nitro-1-benzimidazolecarboxylate
benzyl 2,6-bis(trifluoromethyl)-4-nitro-1-benzimidazolecarboxylate
methyl 2,6-bis(trifluoromethyl)-4-nitro-1-benzimidazolecarboxylate
benzyl 2-(1,1,2,2-tetrafluoroethyl)-4-nitro-6-(trifluoromethyl)-1-benzimidazolecarboxylate
2-ethylhexyl 2-(1,1,2,2-tetrafluoroethyl)-4-nitro-6-(trifluoromethyl)-1-benzimidazolecarboxylate
n-octyl 2-(1,1,2,2-tetrafluoroethyl)-4-nitro-6-(trifluoromethyl)-1-benzimidazolecarboxylate
ethyl 2-(1,1,2,2-tetrafluoroethyl)-4-nitro-6-(trifluoromethyl)-1-benzimidazolecarboxylate
isopropyl 2-(1,1,2,2-tetrafluoroethyl)-4-nitro-6-(trifluoromethyl)-1-benzimidazolecarboxylate
ethyl 2-(chlorodifluoromethyl)-4-nitro-6-(trifluoromethyl)-1-benzimidazolecarboxylate
methyl 2-(1,1,2,2-tetrafluoroethyl)-4-nitro-6-(trifluoromethyl)-1-benzimidazolecarboxylate
2-propenyl 2-(1,1,2,2-tetrafluoroethyl)-4-nitro-6-(trifluoromethyl)-1-benzimidazolecarboxylate
2-propenyl 2-(chlorodifluoromethyl)-4-nitro-6-(trifluoromethyl)-1-benzimidazolecarboxylate
2-hydroxy-2-(1,1,2,2-tetrafluoroethyl)-4-nitro-6-(trifluoromethyl)benzimidazoline, sodium salt
2-hydroxy-2,6-bis(trifluoromethyl)-4-nitrobenzimidazoline, sodium salt
2-isopropoxy-2-(1,1,2,2-tetrafluoroethyl)-4-nitro-6-(trifluoromethyl)benzimidazoline, potassium salt
2-hydroxy-2-(difluoromethyl)-4-nitro-6-chlorobenzimidazoline, calcium salt
2-hydroxy-2-(1,1,2,2-tetrafluoroethyl)-4-nitro-6-(trifluoromethyl)benzimidazoline, calcium salt 2-hydroxy-2-(1,1,2,2-tetrafluoroethyl)-4-nitro-6-(trifluoromethyl)benzimidazoline, silver salt
2-hydroxy-2-(1,1,2,2-tetrafluoroethyl)-4-nitro-6-(trifluoromethyl)benzimidazoline, lithium salt
2-hydroxy-2,6-bis(trifluoromethyl)-4-nitrobenzimidazoline, triethylammonium salt
2-hydroxy-2-(1,1,2,2-tetrafluoroethyl)-4-nitro-6-(trifluoromethyl)benzimidazoline, potassium salt
2-hydroxy-2-(1,1,2,2-tetrafluoroethyl)-4-nitro-6-(trifluoromethyl)benzimidazoline, triethylammonium salt
2-hydroxy-2,6-bis(trifluoromethyl)-4-nitrobenzimidazoline, triethylammonium salt
2-methoxy-2-(pentafluoroethyl)-4-nitro-6-(trifluoromethyl)benzimidazoline, potassium salt
2-ethoxy-2-difluoroethyl-4-nitro-6-chlorobenzimidazoline, potassium salt
2-hydroxy-2-(1,1,2,2-tetrafluoroethyl)-4-nitro-6-(trifluoromethyl)benzimidazoline, ammonium salt
2-hydroxy-2-(1,1,2,2-tetrafluoroethyl)-4-nitro-6-(trifluoromethyl)benzimidazoline, tetraethylammonium salt
2-hydroxy-2-(1,1,2,2-tetrafluoroethyl)-4-nitro-6-(trifluoromethyl)benzimidazoline, tetra-n-butylammonium salt Preferred compounds are those of Formula I. Within Formula I, preferred compounds are those wherein $R^1=CF_3$, and/or $R^5=CF_2H$. Within Formula II, preferred compounds are those wherein $R^7=H$, $R^6=CF_3$, and/or $R^8=CF_2H$.

The compounds to be employed in the present invention are generally known compounds. They are synthesized in accordance with literature methods; see, for example, U.S. Pat. Nos. 3,725,554; 3,755,346; 3,998,465; 4,122,184; and 4,265,901.

The order Hymenoptera, family Formicidae includes the numerous species of ants. The order Isoptera, family Termitidae includes the various species of termites.

Representative species are the following:
Ants (order Hymenoptera, family Formicidae)
Argentine ant—*Iridomyrmex humilis*
Pharaoh ant—*Monomorium pharaonis*
Little black ant—*Monomorium minimum*
Odorous house ant—*Tapinoma sessile*
Thief ant—*Solenopsis molesta*
Cornfield ant—*Lasius alienus*
Pavement ant—*Tetramorium caespitum*
Large yellow ant—*Acanthomyops interjectus*
Small yellow ant—*Acanthomyops claviger*
Black carpenter ant—*Camponotus pennsylvanicus*
Red carpenter ant—*Caponotus ferrugineus*
Florida carpenter ant—*Camponotus abdominalis floridanus*
Brown carpenter ant—*Camponotus castaneus*
Texas leaf-cutting ant—*Atta texana*
Imported fire ant—*Solenopsis geminata*
Black imported fire ant—*Solenopsis richteri*
Red imported fire ant—*Solenopsis invicta*
Southern fire ant—*Solenopsis xyloni*
Leaf cutter ant—*Atta cephalotex*
Leaf cutter ant—*Atta sexdens*
(no common name)—*Acromyrmex* sp.
Big-headed ant—*Pheidole megacephala*

Termites (order Isoptera, family Termitidae)
Eastern subterranean termite—*Reticulitermes flavipes*
Arid-land subterranean termite—*Reticulitermes tibialis*
Western subterranean termite—*Reticulitermes hesperus*
Common dry-wood termite—*Kalotermes minor*
Southern dry-wood termite—*Kalotermes hubbardi*
Southeastern dry-wood termite—*Kalotermes snyderi*
Dry-wood termite—*Kalotermes schwartzi*
Pacific damp-wood termite—*Zootermopsis angusticollis*
Westery dry-wood termite—*Incisitermes minor*
Damp-wood termite—*Paraneotermes simplicornis*
Formosan subterranean termite—*Coptotermes formosanus*
Dry-wood termite—*Criptotermes brevis*
Dry-wood termite—*Criptotermes rospigliosi*
Subterranean termite—*Heterotermes tenuis*
Subterranean termite—*Coptotermes testaceous*
Subterranean termite—*Rhinotermes nasutus*
Tree termite—*Nasutitermes sp.*
(no common name)—*Ancistritermes carithorax*
(no common name)—*Microtermes subhyalinus*

The active agent in accordance with the present invention is employed for the control of ants and termites in manners conventional for the particular species.

In the case of ants, the present active agent is supplied in an edible, preferably attractant bait positioned near the colony or colonies. For ant species which infest pastureland or cropland, an edible bait containing the present active agent can be distributed uniformly on the infested land.

The amount of the present active agent which is effective to eradicate an ant colony will vary with factors such as the identity of the ant; the size and number of the colonies; the mode of application; and other factors. For application to pastureland and cropland, good results are generally obtained by application of from 1 to 100 grams/acre and preferably from 1 to 10 grams/acre; such amounts are readily supplied by applying from 0.05 to 10.00 lbs./acre, preferably 1.0 to 5.0 lbs./acre, of a bait comprising 0.05 to 3.00 percent, and preferably 0.1 to 1.0 percent, of the present active agent. For eradication of isolated colonies, good results are generally achieved with baits containing the present active agent at concentrations of 0.01 to 1.00 percent. In general, it is desirable to use a minimum effective amount, to minimize exposure to non-target species.

Baits containing the present active agent can be prepared in manners conventional for the species to be controlled. For many ant species, including fire ants, the active agent is dissolved in an oil or fat. The oil or fat can be a vegetable oil such as soybean oil, sesame seed oil, coconut oil, cottonseed oil, safflower oil, peanut oil, or corn oil; or an animal fat such as lard or tallow. Because of its low cost and ready availability, soybean oil is generally preferred. The solution can be supplied as such but is preferably distributed on a carrier such as puffed corn, corncob grits, starch, or the like. In general, any adsorbent material with adequate oil capacity, such as 15 percent or greater, which is not offensive to ants, is acceptable. Pregelled defatted corn grits has been found to be preferable because of its higher oil capacity.

The bait can also include an attractant, such as lecithin or any nutritive substance with particular appeal to the ant species.

In the case of termites, repellency is a more important mode of control. Termite control typically takes the form of treating soil surrounding houses and other buildings sought to be protected against termites, although other conventional methods of application can also be employed with the present active agent.

For termite control, the present active agent is formulated in conventional manners. The agent can be dissolved in a solvent or formulated as a water emulsion, for application to soil. For example, the present active agent can be formulated as a wettable powder, e.g.,

| | |
|---|---|
| 2-(1,1,2,2-tetrafluoroethyl)-4-nitro-6-(trifluoromethyl)benzimidazole | 50% |
| Stepanol ME (Stepan Chemical Co. brand of sodium lauryl sulfate) | 5% |
| Polyfon O (an anionic surfactant sold by Westvaco Corporation Polychemicals Dept. and comprising a sodium lignosulfonate) | 5% |
| Zeolex 7 (a sodium silicoaluminate sold by J. M. Huber Corp.) | 5% |
| Bardens Clay | 35% |
| or as an emulsifiable concentrate, e.g., | |
| 2-(1,1,2,2-tetrafluoroethyl)-4-nitro-6-(trifluoromethyl)benzimidazole | 25% |
| acetophenone | 63% |
| Sponto 1003 (a surfactant sold by Witco Chemical, comprising a blend of oil-soluble metal sulfonates and polyoxyethylene ethers) | 12% |

The wettable powder or emulsifiable concentrate can then be dispersed in water to constitute a soil-treating formulation. Similarly, the present active agent can be dissolved in a solvent, including aromatics such as xylene, toluene, and aromatic naphthas; alcohols; esters; and acetonitrile, to constitute a soil-treating formulation. Certain of the present benzimidazolines, such as the sodium salts, are sufficiently soluble in water that they are readily formulated as water solutions.

The present active agent generally gives effective termite control when employed in formulations comprising from 0.05 to 1.0% of active agent, applied at standard termite control application rates such as 1 gallon per 5–10 sq. ft. and 1 gallon per 2½–5 lineal ft.

The practice of the present invention is illustrated by the following examples.

EXAMPLE 1: INDIVIDUAL ANT FEEDING TEST 2-(1,1,2,2-Tetrafluoroethyl)-4-nitro-6-(trifluoromethyl) benzimidazole was evaluated for the control of the red imported fire ant (*Solenopsis invicta*, variety Buren). Four separate tests were conducted, each under laboratory conditions, with worker ants.

Each test was conducted in 30 ml. disposable plastic medicine cups (40 mm internal dimension at the top, tapering to 32 mm internal dimension at the bottom, 38 mm high). A hole (6 mm diam.) was drilled through the bottom of each cup and a layer of plaster of Paris and builders' cement (9:1 ratio) was poured over the bottom. The plaster mixture covered the hole and acted as a wick to draw up water when the cup was placed on a wet peat moss bed. (Moisture is necessary to keep the humidity in the cups high and thereby prevent desiccation of the ants. The cement is added to make a hard mixture through which the ants cannot tunnel and escape).

Twenty worker ants from field-collected colonies were placed in each test chamber ca. 24 hours preceding start of the test. This pretreatment holding period allowed time for recovery of the ants from handling and for orientation to the containers.

The candidate compound was dissolved directly in the food material, soybean oil. The toxic solution was offered to the ants on cotton swabs saturated with the material and placed in the test chamber in small vial caps.

The ants were allowed to feed as desired on the toxic bait for 24 hours. After this exposure period, the toxicant was removed from the chamber and the ants remained without food for an additional 24 hours. At the end of this time new vial caps containing cotton swabs saturated with soybean oil were placed in the chamber and left for the remainder of the test period. Knockdown and mortality counts were made at intervals of 1, 2, 3, 6, 8, 10, 13 and 14 days following initial exposure. Each test consists of three replications. Room temperature was maintained at 80± F.

Results were as reported in the following table.

TABLE I

| Treatment | No. of tests[a] | Concn. of compound in soybean oil (%) | Average percent knockdown and kill after indicated no. of days | | | | | | |
|---|---|---|---|---|---|---|---|---|---|
| | | | 1 | 2 | 3 | 6 | 8 | 10 | 14 |
| 2-(1,1,2,2-tetrafluoroethyl)-4-nitro-6-(trifluoromethyl)-benzimidazole | 4 | 0.01 | 1 | 2 | 14 | 55 | 67 | 77 | 85 |
| | | 0.1 | 76 | 92 | 95 | 98 | 99 | 99 | 100 |
| | | 1.0 | 88 | 96 | 99 | 100 | | | |
| Mirex (standard) | 4 | 0.01 | 0 | 1 | 1 | 7 | 19 | 34 | 58 |
| | | 0.1 | 1 | 2 | 17 | 66 | 84 | 92 | 100 |
| | | 1.0 | 0 | 57 | 90 | 100 | | | |
| Soybean oil (check) | 4 | | 0 | 2 | 3 | 7 | 9 | 11 | 16 |

[a]Each test consisted of 3 replicates at each concentration, with 20 worker ants per replicate.

EXAMPLE 2: INDIVIDUAL ANT FEEDING TESTS

Two additional compounds were tested in the procedures of Example 1. Only one test was conducted with each compound, with each test consisting of three replicates at each concentration, with 20 worker ants per replicate. The results were as set forth in the following table.

TABLE II

| Treatment | Concn. of compound in soybean oil (%) | Precent knockdown and kill after indicated no. of days | | | | | | |
|---|---|---|---|---|---|---|---|---|
| | | 1 | 2 | 3 | 6 | 8 | 10 | 14 |
| Isopropyl 2-(chlorodifluoro- | 0.01 | 2 | 3 | 3 | 3 | 3 | 7 | 15 |

TABLE II-continued

| Treatment | Concn. of compound in soybean oil (%) | Precent knockdown and kill after indicated no. of days | | | | | | |
|---|---|---|---|---|---|---|---|---|
| | | 1 | 2 | 3 | 6 | 8 | 10 | 14 |
| methyl)-4-nitro-6-(trifluoro-methyl)-1-benzimidazole-carboxylate | 0.1 | 20 | 50 | 58 | 95 | 97 | 98 | 98 |
| | 1.0 | 100 | | | | | | |
| Isopropyl 2-(1,1,2,2-tetra-fluoroethyl)-4-nitro-6-(trifluoromethyl)-1-benzimidazolecarboxylate | 0.01 | 0 | 2 | 7 | 40 | 57 | 68 | 93 |
| | 0.1 | 68 | 90 | 95 | 98 | 98 | 98 | 100 |
| | 1.0 | 100 | | | | | | |
| Mirex (standard) | 0.01 | 0 | 2 | 5 | 8 | 55 | 87 | 100 |
| | 0.1 | 0 | 0 | 5 | 85 | 85 | 100 | |
| | 1.0 | 2 | 80 | 100 | | | | |
| Soybean oil (check) | — | 0 | 1 | 2 | 3 | 3 | 3 | 4 |

EXAMPLES 3-4: INDIVIDUAL ANT GAVAGE TESTS

Each of two of the compounds to be employed in accordance with the present invention was administered by gavage to groups of red imported fire ants (Solenopsis invicta) and the ants were observed for seven days to determine toxicity. Each compound was dissolved in soybean oil and 0.1 microliter of the solution was administered to each ant by gavage; the concentration of compound in the solution varied. The ants were observed for seven days and the number of ants dead on each day counted, and converted into percent dead for that day. The results of these tests are reported in the following table.

TABLE III

| Compound | Nanograms of Compound Delivered to Each Ant | Percent Dead per Day | | | | | | |
|---|---|---|---|---|---|---|---|---|
| | | 1 | 2 | 3 | 4 | 5 | 6 | 7 |
| 2-(1,1,2,2-tetra-fluoroethyl)-4-nitro-6-(trifluoro-methyl)benzimidazole | 10 | 0 | 5 | 10 | 5 | 14 | 14 | 5 |
| | 25 | 0 | 16 | 26 | 16 | 0 | 11 | 5 |
| | 50 | 22 | 39 | 6 | 11 | 0 | 6 | 0 |
| 2-hydroxy-2-(1,1,2,2-tetra-fluoroethyl)-4-nitro-6-(trifluoro-methyl)benzimidazo-line, sodium salt | 10 | 5 | 19 | 14 | 10 | 0 | 5 | 19 |
| | 25 | 18 | 27 | 14 | 14 | 5 | 9 | 5 |
| | 50 | 35 | 22 | 17 | 13 | 4 | 4 | 4 |
| | 75 | 61 | 11 | 6 | 17 | 0 | 0 | 0 |
| | 100 | 60 | 20 | 10 | 5 | 5 | | |

EXAMPLES 5-6: LABORATORY COLONY FEEDING TESTS

Each of two compounds to be employed in accordance with the present invention was evaluated for the control of laboratory colonies of red imported fire ants (Solenopsis invicta). Colonies were brought in from the field, acclimated to laboratory conditions, and then used in testing. Each compound was dissolved in soybean oil and the solution mixed with pregelled defatted corn grits; the final bait contained 0.4 percent of the respective compound. The bait was supplied to the colony for two weeks and the colony observed for toxicity at 1, 2, and 3 days and at two weeks. The cumulative toxicity observed was as set forth in the following table.

TABLE IV

| Compound | Cumulative Toxicity | | | |
|---|---|---|---|---|
| | 1 day | 2 days | 3 days | 2 weeks |
| 2-(1,1,2,2-tetrafluoro-ethyl)-4-nitro-6-(tri-fluoromethyl)benzimida-zole | 50 | 66 | 75 | 95 |
| 2-hydroxy-2-(1,1,2,2-tetra-fluoroethyl)-4-nitro-6-(trifluoromethyl)-benzimidazoline, sodium salt | 40 | 57 | 64 | 93 |
| Control | 0.5 | 0.8 | 1.2 | 18.2 |

EXAMPLES 7-8: LABORATORY COLONY FEEDING TESTS

The procedures of Examples 5-6 were repeated except that observations for toxicity were made only through eight days. The results were as follows:

TABLE V

| Compound | Cumulative Toxicity | | | | |
|---|---|---|---|---|---|
| | 1 day | 2 days | 3 days | 7 days | 8 days |
| 2-(1,1,2,2-tetra-fluoroethyl)-4-nitro-6-(trifluoromethyl)-benzimidazole | 54 | 71 | 81 | 89 | 93 |
| 2-hydroxy-2-(1,1,2,2-tetrafluoroethyl)-4-nitro-6-(trifluoro-methyl)benzimidazo-line, sodium salt | 94 | 99 | 100 | 100 | 100 |

I claim:

1. Method for eradicating a red imported fire ant colony, which comprises supplying to the colony an effective amount of an active agent which is selected from the class consisting of compounds of the formulae

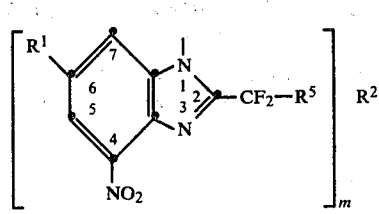

and

-continued

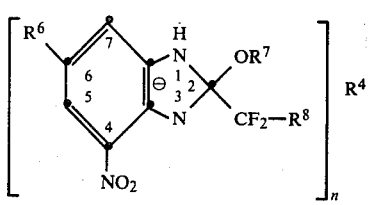

wherein $R^1$–$R^8$ and m and n have the following meanings:

$R^1$ = halo, $CF_3$, $CF_2H$, or $CF_2Cl$;

$R^2$ = H, $COOR^3$, or $R^4$;

$R^3$ = alkyl of $C_1$–$C_8$, alkenyl of $C_3$–$C_4$, or benzyl;

$R^4$ = sodium, potassium, lithium, silver, magnesium, calcium, barium, strontium, ammonium, or substituted ammonium derived from an organic amine which is as basic as, or more basic than, ammonia:

$R^5$ = H, Cl, F, $CF_2H$, or $CF_3$;

$R^6$ = Br, Cl, or $CF_3$;

$R^7$ = H or lower alkyl of $C_1$–$C_4$;

$R^8$ = H, F, $CF_2H$, or $CF_3$;

m = when $R^2$ = H or $COOR^3$, 1, and when $R^2$ = $R^4$, the valence of $R^4$; and n = the valence of $R^4$.

2. The method of claim 1 wherein the active agent is a compound of Formula I.

3. The method of claim 2 wherein in the active agent $R^1$ = $CF_3$ and $R^5$ = $CF_2H$.

4. The method of claim 3 wherein the active agent is 2-(1,1,2,2-tetrafluoroethyl)-4-nitro-6-(trifluoromethyl)-benzimidazole.

5. The method of claim 3 wherein the active agent is 2-(1,1,2,2-tetrafluoroethyl)-4-nitro-6-(trifluoromethyl)-benzimidazole, sodium salt.

6. The method of claim 3 wherein the active agent is 2-(1,1,2,2-tetrafluoroethyl)-4-nitro-6-(trifluoromethyl)-benzimidazole, ammonium salt.

7. The method of claim 4 wherein the active agent is 2-(1,1,2,2-tetrafluoroethyl)-4-nitro-6-(trifluoromethyl)-benzimidazole, triethylammonium salt.

8. The method of claim 2 wherein the active agent is 2,6-bis(trifluoromethyl)-4-nitrobenzimidazole.

9. The method of claim 1 wherein the active agent is a compound of Formula II.

10. The method of claim 9 wherein in the active agent $R^7$ = H.

11. The method of claim 10 wherein in the active agent $R^6$ = $CF_3$ and $R^8$ = $CF_2H$.

12. The method of claim 11 wherein the active agent is 2-hydroxy-2-(1,1,2,2-tetrafluoroethyl)-4-nitro-6-(trifluoromethyl)benzimidazoline, sodium salt.

13. The method of claim 11 wherein the active agent is 2-hydroxy-2-(1,1,2,2-tetrafluoroethyl)-4-nitro-6-(trifluoromethyl)benzimidazoline, potassium salt.

14. The method of claim 11 wherein the active agent is 2-hydroxy-2-(1,1,2,2-tetrafluoroethyl)-4-nitro-6-(trifluoromethyl)benzimidazoline, ammonium salt.

15. The method of claim 10 wherein in the active agent, $R^6$ = $CF_3$ and $R^8$ = F.

* * * * *